United States Patent [19]

Ichihashi et al.

[11] 4,442,101

[45] Apr. 10, 1984

[54] SESQUIHYDRATE OF NAPHTHYRIDINE DERIVATIVE, AND PROCESS FOR THE PREPARATION THEREOF

[75] Inventors: Hitoshi Ichihashi, Kyoto; Terukazu Tanaka, Osaka; Yu Imasato, Toyonaka, all of Japan

[73] Assignees: Dainippon Pharmaceutical Co., Ltd., Osaka, Japan; Laboratoire Roger Bellon, Neuilly sur Seine, France

[21] Appl. No.: 345,916

[22] Filed: Feb. 4, 1982

[30] Foreign Application Priority Data

Feb. 13, 1981 [JP] Japan .................................. 56-20749

[51] Int. Cl.³ .................. C07D 487/04; A61K 31/495
[52] U.S. Cl. .................................... 424/250; 544/362; 544/363
[58] Field of Search ................. 544/362, 363; 424/250

[56] References Cited

U.S. PATENT DOCUMENTS

| | | | |
|---|---|---|---|
| 3,149,104 | 9/1964 | Lesher et al. | 544/362 |
| 3,590,036 | 6/1971 | Lesher et al. | 544/362 |
| 3,849,421 | 11/1974 | Nakagome et al. | 544/362 |
| 4,017,622 | 4/1977 | Minami et al. | 544/362 |
| 4,146,719 | 3/1979 | Irikura | 544/362 |
| 4,352,803 | 10/1982 | Matsumoto et al. | 544/363 |
| 4,359,578 | 11/1982 | Matsumoto et al. | 544/363 |

FOREIGN PATENT DOCUMENTS

| | | | |
|---|---|---|---|
| 58614 | 8/1982 | European Pat. Off. | 544/362 |
| 2939786 | 4/1980 | Fed. Rep. of Germany | 544/363 |
| 2034698 | 6/1980 | United Kingdom | 544/363 |

OTHER PUBLICATIONS

Yuasa, R. et al., Yakugaku Zasshi, 102 (5), 469–476, (1982) "Pharmaceutical Studies on Hydrates of Am–715, Physical Characteristics and Intestinal Absorption."

*Primary Examiner*—Mary C. Lee
*Assistant Examiner*—S. A. Gibson
*Attorney, Agent, or Firm*—Wenderoth, Lind & Ponack

[57] ABSTRACT

Novel 1-ethyl-6-fluoro-1,4-dihyono-4-oxo -7-(1-piperazinyl)-1,8-naphthyridine-3-carboxylic acid.sesquihydrate (ATT-2266.sesquihydrate). The aforesaid compound can be prepared by heating 1-ethyl-6-fluoro-1,4-dihydro-4-oxo -7-(1-piperazinyl)-1,8-naphthyridine-3-carboxylic acid at a temperature above about 60° C. in the presence of water in an amount sufficient to form the sesquihydrate. This sesquihydrate is much more stable than the anhydrate and the trihydrate and is superior to the anhydrate in the rate of dissolution and transference into the body through the intestines. Thus, it is especially useful as a pharmaceutical compound.

11 Claims, 7 Drawing Figures

Fig. 1

Fig. 2 IR SPECTRUM OF SESQUIHYDRATE

Fig. 3 IR SPECTRUM OF ANHYDRATE

Fig. 4  IR SPECTRUM OF TRIHYDRATE

Fig. 6

THERMAL ANALYSIS OF ANHYDRATE

Fig. 7

THERMAL ANALYSIS OF TRIHYDRATE

SESQUIHYDRATE OF NAPHTHYRIDINE DERIVATIVE, AND PROCESS FOR THE PREPARATION THEREOF

BACKGROUND OF INVENTION

The present invention relates to novel 1-ethyl-6-fluoro-1,4-dihydro-4-oxo-7-(1-piperazinyl)-1,8-naphthyridine-3-carboxylic acid.sesquihydrate, processes for the preparation thereof, a pharmaceutical composition containing it and also its use.

1-Ethyl-6-fluoro-1,4-dihydro-4-oxo-7-(1-piperazinyl)-1,8-naphthyridine-3-carboxylic acid (this compound is sometimes referred to as "AT-2266" hereinafter) is expressed by the following structural formula.

Methods for synthesizing the AT-2266 and the usefulness of the AT-2266 as a chemotherapeutic agent were already disclosed in the specification of European Laid-Open Patent Publication No. 9425, Apr. 2, 1980, Bulletin Number 80/7. The European Patent Specification generally describes that the AT-2266, etc. may exist in the form of a hydrate, but fails to give any specific description about the AT-2266 hydrate.

British Laid-Open Patent Publication No. 2034698 A discloses AT-2266 and its hydrates and acid addition salts. No specific statement is made, however, about methods for producing AT-2266 and its hydrates.

The present inventors have continued to study the physical and chemical properties of the AT-2266 and found that AT-2266 can exist in the form of a trihydrate as well as in anhydrous form. Specifically, they have found that contacting of anhydrous AT-2266 (this compound is sometimes referred to as "anhydrate" hereinafter) with water at room temperature results in the ready conversion of the anhydrate into AT-2266.trihydrate (this compound is sometimes referred to as "trihydrate" hereinafter) and the trihydrate is converted back into the anhydrous form by drying it. Moreover, both the anhydrate and the trihydrate have been found to be unstable to light.

Hence, in the preparation of these compounds and pharmaceutical preparations, such as tablets, containing these compounds, the operations must be carried out under shielding of light with sufficient attention to absorption or desorption of water of crystallization. During storage and handling, too, these products must be protected from light, heat and/or atmospheric moisture. More specifically, a room in which to handle the anhydrate must be kept at the lowest possible humidity, and conversely, a room in which to handle the trihydrate must be kept at the lowest possible temperature and the highest possible humidity. Moreover, these rooms should be as dark as possible, and preferably darkrooms. Unless all of these conditions are provided, these compounds or preparations containing these compounds would change in weight, and/or turn yellow, and thus would not serve for practical purposes and would lose their commercial value.

In particular, difficulty is encountered in the production of pharmaceutical preparations such as tablets which contain the trihydrate because all of the steps of production must be carried out under conditions which do not cause the loss of its water of crystallization. For example, even when the trihydrate is used in preparing tablets, its water of crystallization is lost during a drying step usually carried out at 40°–50° C., and tablets containing only the trihydrate cannot be obtained. The resulting tablets contain either a mixture of the anhydrate and the trihydrate or only the anhydrate.

Accordingly, these compounds still have great defects.

DETAILED DESCRIPTION OF THE INVENTION

The present inventors furthered their studies on these compounds, and finally found that AT-2266.sesquihydrate is unexpectedly much more stable than the anhydrate and the trihydrate.

It has been ascertained by X-ray diffraction analysis, IR spectrum, thermal analysis, etc. that the AT-2266.sesquihydrate (this compound may sometimes be abbreviated as "sesquihydrate" hereinafter) of the present invention is definitely different from the anhydrate and the trihydrate. As will be described below in greater detail, the AT-2266.sesquihydrate is much more stable to heat, changes of humidity, light, etc. than the anhydrate and the trihydrate, and is superior to the anhydrate in the rate of dissolution and transference into the body through the intestines. Thus, the compound of the invention is especially valuable as a pharmaceutical compound.

(1) The compound of the present invention, the AT-2266 sesquihydrate, is prepared as follows:

It is prepared by heating the AT-2266 at a temperature of above about 60° C. in the presence of water in an amount sufficient to form the sesquihydrate. In the case of using the trihydrate as the raw material, it can be converted into the sesquihydrate by heating it without external addition of water so long as the heating is effected in a sealed vessel such as a sealed tube. To convert the anhydrate into the sesquihydrate, water is required in an amount of at least 1.5 equivalents per equivalent of the anhydrate. Advantageously, the heating is carried out in the presence of an excess of water irrespective of which raw material is to be used. Water may be caused to be present in the form of a liquid, moisture, wet or dry steam, or the like.

Investigations of the present inventors have shown that when heated, the AT-2266 and the AT-2266.trihydrate begin to form crystals of the AT-2266.sesquihydrate at above about 60° C. Accordingly, the sesquihydrate is a very special crystal, and in the production of the sesquihydrate, energy corresponding to a temperature of at least about 60° C. must be applied to AT-2266 (anhydrate or trihydrate) in the presence of a suitable amount of water. Otherwise, the transformation to the sesquihydrate crystals would not occur. The heating temperature is at least about 60° C. and up to the minimum temperature at which AT-2266 is decomposed. Thus, there is no particular restriction on the upper limit of the heating temperature, but heating to a temperature of more than 160° C. is not particularly advantageous. Generally, the heating temperature is about 60° to about 160° C., preferably 61° to about 130° C., especially preferably about 70° to about 100° C. When the heating temperature is more than 100° C., the heating is preferably carried out in a closed atmosphere. The heating time varies greatly depending upon the heating temperature and/or the amount of water. Usually, it is 5 minutes to 5 weeks.

Some preferred embodiments of production are given below.

(i) The anhydrous AT-2266 or the AT-2266.trihydrate is heated at a temperature above about 60° C. and a relative humidity above 30% to give the AT-2266.sesquihydrate. The rate of conversion into the sesquihydrate increases with increasing relative humidity. While the heating period is variable according to the humidity, heating temperature, etc., it takes 30 minutes to 5 weeks to complete the transformation. Expecially when the reaction is carried out with heating in an autoclave in the presence of moisture, the sesquihydrate is prepared in shorter periods. The resulting product is dried at a temperature below 80° C. for elimination of the adhering water to give the final product.

(ii) The anhydrous AT-2266 or the trihydrate is suspended in water kept at a temperature above about 60° C. and is sufficiently contacted with water to give the sesquihydrate, too. The heating period, depending on the temperature, is usually 10 minutes to 5 hours. The reaction is preferably carried out with stirring to accelerate the transformation. The resulting crystals are separated from the solvent and dried in the same way as described above to give the final product.

(iii) The anhydrous AT-2266 or the trihydrate is dissolved in an aqueous alkaline solution or acidic solution, and the solution is neutralized with an acid or alkali on heating at a temperature above about 60° C. to give the sesquihydrate as crystals. It is preferable to keep the suspension heating for a while after neutralization. The resulting product is separated from the solvent and dried at a temperature below 80° C. to give the final product. Alternatively, a salt of the AT-2266 (sodium salt, hydrochloride, acetate, methanesulfonate, etc.) prepared separately may be used as the starting material. In this case the salt is dissolved in water, and the solution is kept at a temperature above about 60° C. and neutralized with an acid or alkali in the same way as described above to give the sesquihydrate.

The starting materials used in the above methods except the salt may be a mixture of the anhydrous form and the trihydrate or the trihydrate with adhering water.

Figure 1:
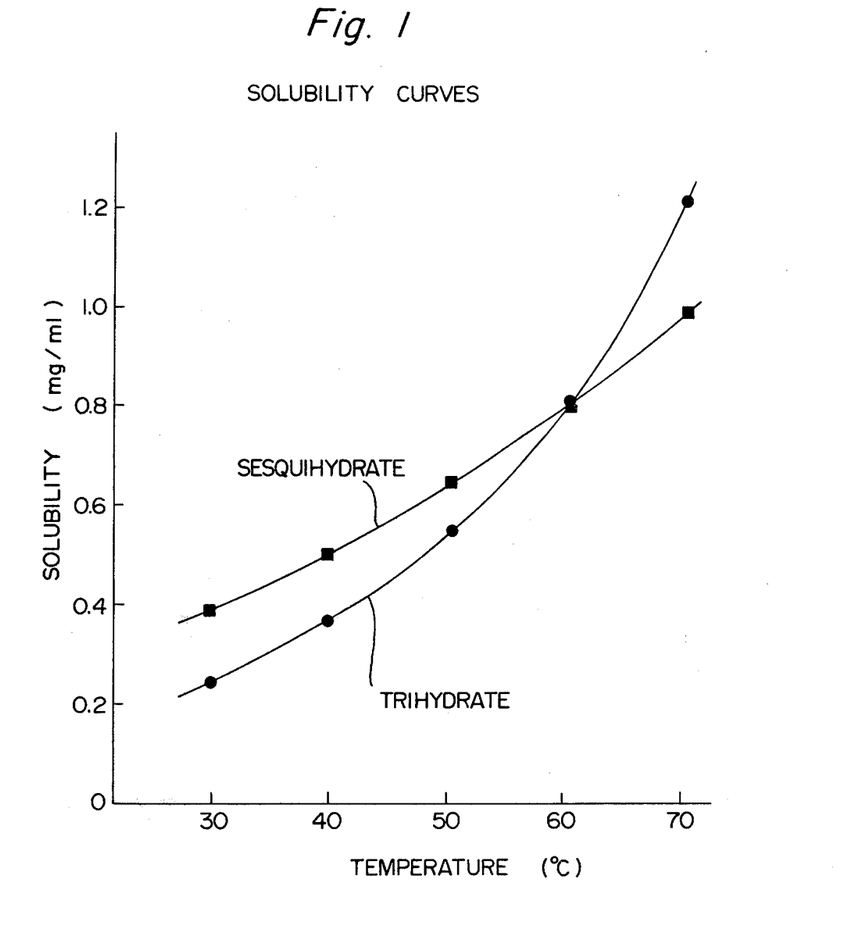
FIG. 1 shows solubility curves for AT-2266.trihydrate and AT-2266.sesquihydrate.

The sesquihydrate is prepared as mentioned above, and theoretically the mechanism of formation of the sesquihydrate will be understood from the water solubility curves shown in FIG. 1. The solubility of the AT-2266.sesquihydrate in water is less than that of the trihydrate at a temperature above about 60° C., but at a temperature below about 60° C. it is reversed. Therefore, the sesquihydrate is always separated as crystals as far as the crystallization is carried out under conditions in which the solubility of the AT-2266.sesquihydrate in water is less than that of the trihydrate even if any form of the compounds is dissolved in. On the contrary as far as the crystallization is carried out under conditions in which the solubility of the AT-2266.trihydrate is less than that of the sesquihydrate, the trihydrate is always separated as crystals, and the sesquihydrate is never produced.

(2) The physical properties of the sesquihydrate are described below in comparison with those of the trihydrate and the anhydrate.

Figure 2:
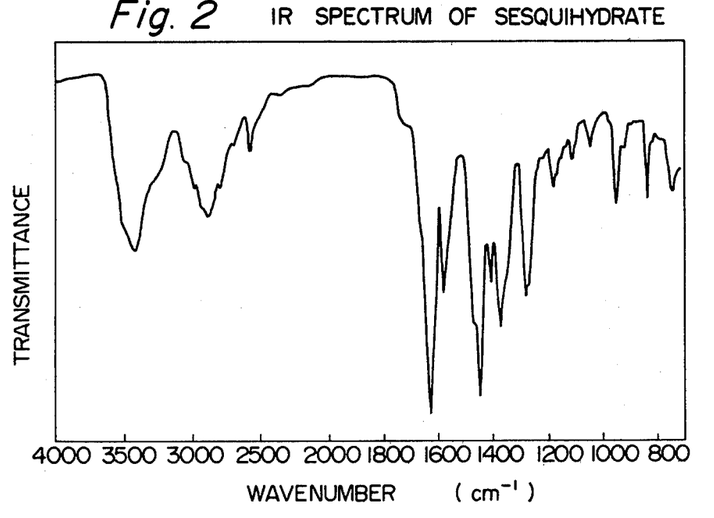
FIG. 2 is an IR spectrum of AT-2266.sesquihydrate.
Figure 3:
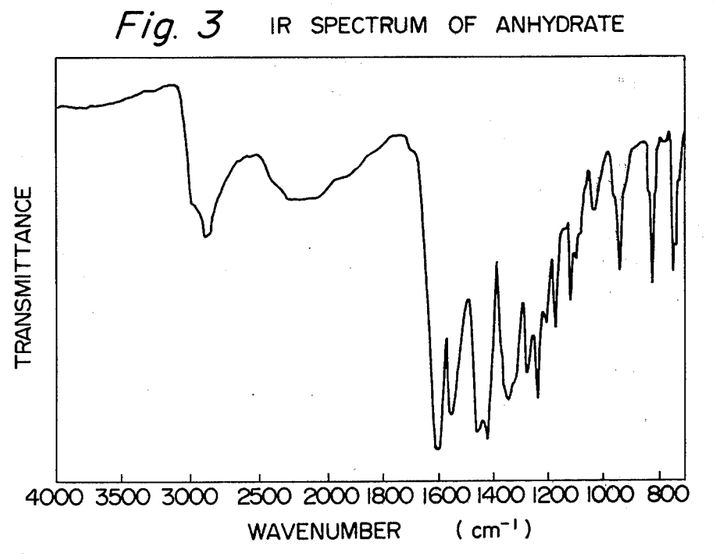
FIG. 3 is an IR spectrum of AT-2266.anhydrate.
Figure 4:
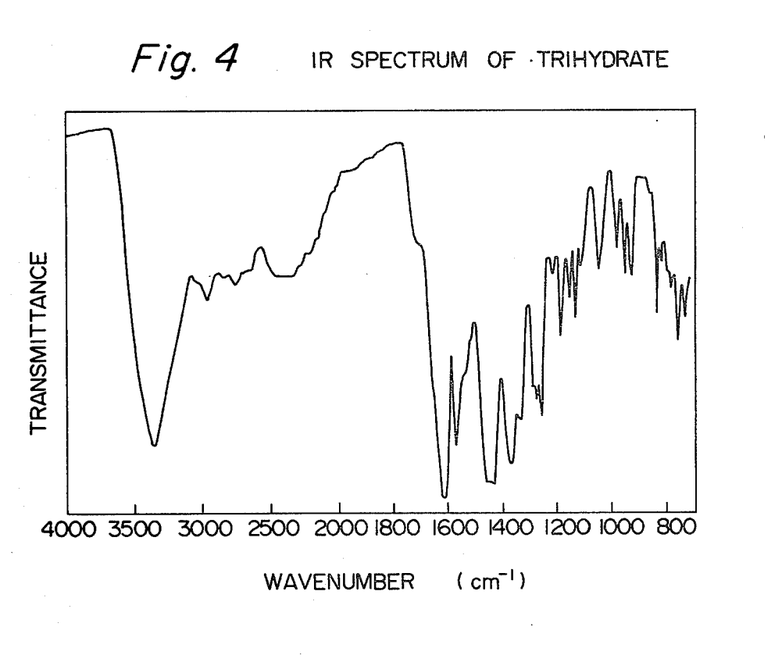
FIG. 4 is an IR spectrum of AT-2266.trihydrate.
Figure 5:
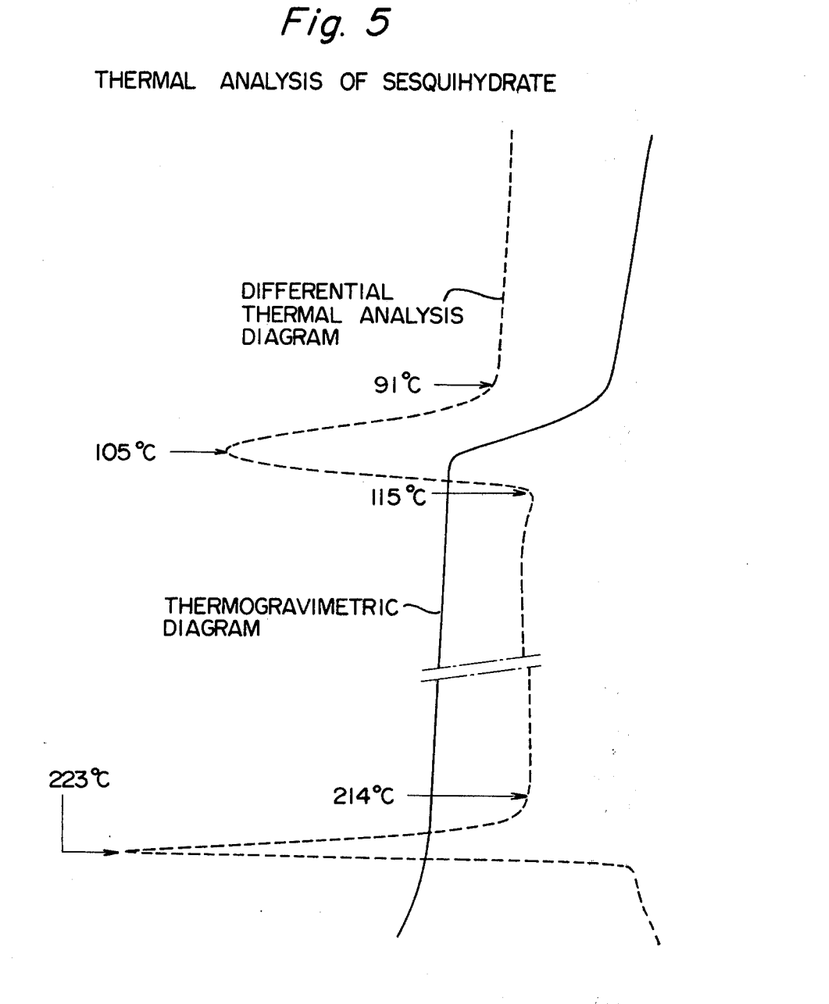
FIG. 5 is a thermal analysis of AT-2266.sesquihydrate.
Figure 6:
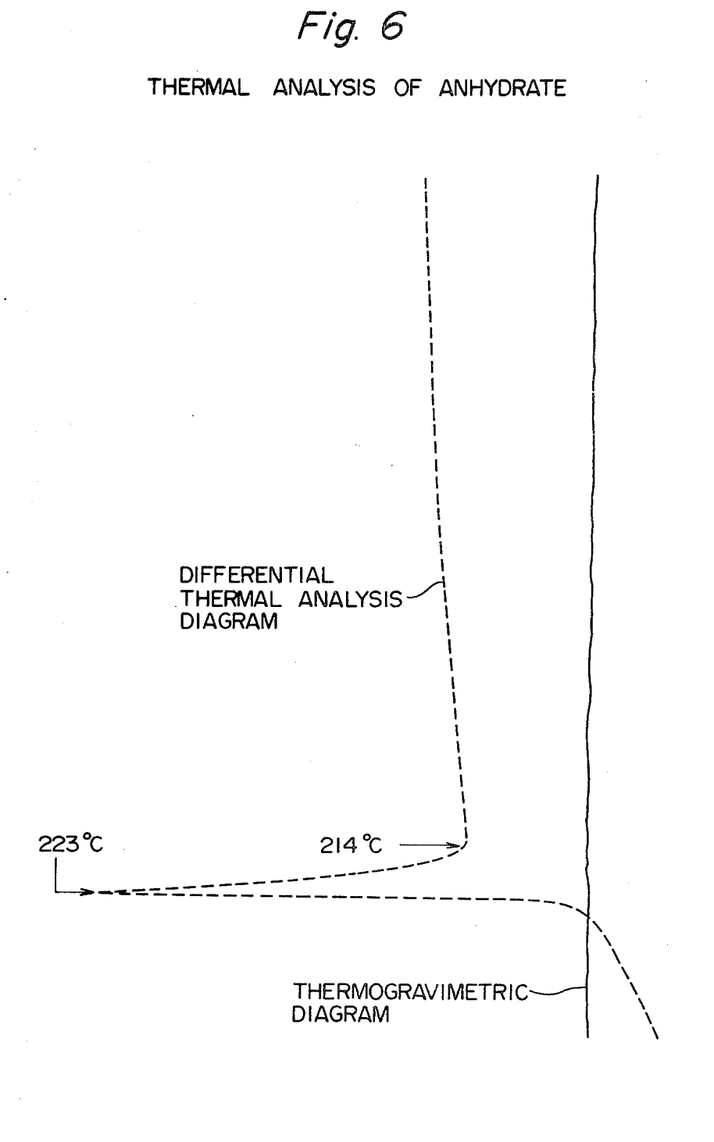
FIG. 6 is a thermal analysis of AT-2266.anhydrate.
Figure 7:
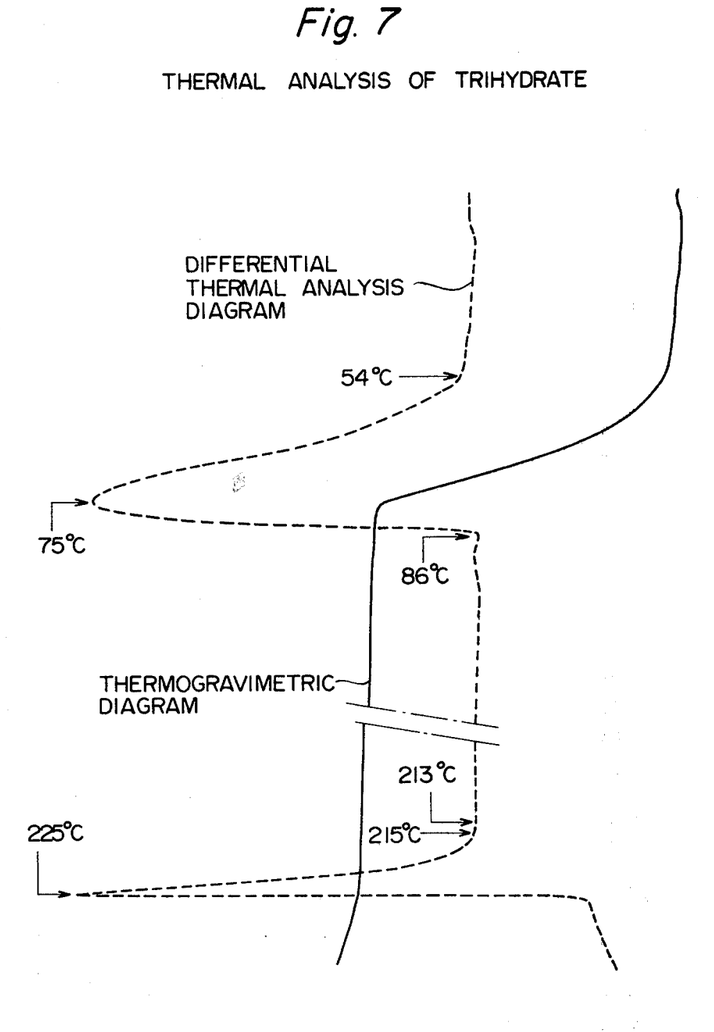
FIG. 7 is a thermal analysis of AT-2266.trihydrate.

| | AT-2266 | | |
|---|---|---|---|
| | sesquihydrate 220–224° C. | anhydrate 220–224° C. | trihydrate 220–224° C. |
| m.p. | | | |
| elemental analysis | corresponding to $C_{15}H_{17}N_4O_3F$ .1.5$H_2O$ | corresponding to $C_{15}H_{17}N_4O_3F$ | corresponding to $C_{15}H_{17}N_4O_3F$ 3$H_2O$ |
| IR spectrum (KBr) | shown in FIG. 2 | shown in FIG. 3 | shown in FIG. 4 |
| thermal* analysis | shown in FIG. 5 | shown in FIG. 6 | shown in FIG. 7 |
| X-ray diffraction | shown in Table 1 | shown in Table 2 | shown in Table 3 |

*Experimental conditions of thermal analysis:
Sample weight: 11.70 mg (sesquihydrate) 9.80 mg (anhydrate) 10.81 mg (trihydrate)
Heating rate: 5° C./min.
Atmosphere: in the air
Standard substance: α-$Al_2O_3$

TABLE 1

| X-ray powder diffraction of the AT-2266.sesquihydrate | | | |
|---|---|---|---|
| 2θ | I/Io | 2θ | I/Io |
| 7.9 | 1.00 | 20.9 | 0.28 |
| 10.3 | 0.20 | 21.3 | 0.09 |
| 11.1 | 0.13 | 22.5 | 0.07 |
| 11.6 | 0.09 | 23.7 | 0.13 |
| 13.0 | 0.26 | 24.2 | 0.24 |
| 13.5 | 0.40 | 25.6 | 0.74 |
| 15.9 | 0.55 | 26.4 | 0.07 |
| 17.6 | 0.06 | 27.3 | 0.12 |
| 19.3 | 0.26 | 29.9 | 0.12 |

Experimental conditions:
Cu(Kα, λ = 1.5405 Å): Ni,
Electric power source: 15 KV, 20 mA

TABLE 2

| X-ray powder diffraction of the anhydrous AT-2266 | | | |
|---|---|---|---|
| 2θ | I/Io | 2θ | I/Io |
| 10.1 | 0.10 | 22.4 | 0.25 |
| 11.1 | 0.62 | 23.3 | 0.28 |
| 14.7 | 1.00 | 24.4 | 0.87 |
| 17.2 | 0.30 | 26.1 | 0.28 |
| 19.8 | 0.30 | 27.3 | 0.08 |
| 20.4 | 0.21 | 28.6 | 0.10 |
| 21.4 | 0.13 | 29.3 | 0.08 |
| 21.9 | 0.13 | | |

Experimental conditions: same as in Table 1

TABLE 3

| X-ray powder diffraction of the AT-2266.trihydrate | | | |
|---|---|---|---|
| 2θ | I/Io | 2θ | I/Io |
| 10.1 | 1.00 | 24.1 | 0.47 |
| 12.9 | 0.14 | 24.6 | 0.17 |
| 15.7 | 0.17 | 25.1 | 0.40 |
| 18.4 | 0.09 | 26.3 | 0.24 |
| 19.4 | 0.13 | 27.4 | 0.12 |
| 19.7 | 0.15 | 28.0 | 0.12 |
| 20.7 | 0.12 | 28.5 | 0.15 |
| 22.1 | 0.05 | 29.1 | 0.08 |

TABLE 3-continued

| X-ray powder diffraction of the AT-2266.trihydrate | | | |
|---|---|---|---|
| 2θ | I/Io | 2θ | I/Io |
| 22.7 | 0.07 | 29.5 | 0.10 |

Experimental conditions: same as in Table 1

As the result of thermal analysis of each powdered compound, the differential thermal analysis diagram of the anhydrate shows a single endothermic peak at 224° C. (melting with decomposition). The differential thermal analysis diagram of the trihydrate shows two endothermic peaks at 47° C.–86° C. (lower temperature side peak) and at the same temperature as that of the anhydrate (higher temperature side peak) and the thermal change at the lower temperature accompanies the release of its water crystallization and at that temperature the thermogravimetric diagram gives a decrease of weight corresponding to three mols water (−14.4%). The differential thermal analysis diagram of the sesquihydrate shows two endothermic peaks at 90° C.–115° C. (lower temperature side peak) and at the same temperature as that of the anhydride (higher temperature side peak) and the thermal change at the lower temperature accompanies the release of water of crystallization and at that temperature the thermal diagram gives a decrease of weight corresponding to 1.5 mols water (−7.8%). Some of these results are shown in FIGS. 5, 6 and 7.

As shown in X-ray powder diffraction spectrum (Tables 1, 2 and 3), characteristic peaks of the sesquihydrate are 7.9°, and 25.6° at 2θ, those of the anhydrate are 11.1°, 14.7° and 24.4° at 2θ, and that of the trihydrate is 10.1° at 2θ. Judging from their spectrum, these compounds are recognized to have clearly different crystal structures from each other.

As shown in the above data, the compound of the present invention, the sesquihydrate is not an amorphous form of hydrate and further it is undoubtly different from the trihydrate as well as from the anhydrate. From the results of the thermal analysis, etc., moreover, it is also found that the sesquihydrate is neither an intermediate of the transition from the anhydrate to the trihydrate nor from the trihydrate to the anhydrate.

(3) The stability of the AT-2266.sesquihydrate is explained below.

(i) Effect of light

The colouring degree [colour difference ΔE (L, a, b)] of the each powder exposed to light of a fluorescent lamp was measured agingly. The results are shown in the following Tables.

TABLE 4

|  | 30 min | 2 hrs | 3 hrs | 7 hrs | 11 hrs | 28 hrs |
|---|---|---|---|---|---|---|
| sesquihydrate | 1.0 | 2.3 | 3.0 | 4.3 | 5.2 | 8.4 |
| anhydrate | 8.7 | 13.7 | 15.4 | 18.4 | 19.4 | 22.0 |
| trihydrate | 3.0 | 6.7 | 7.6 | 11.1 | 13.0 | 19.2 |

Experimental conditions:
Light; 5,000 lux (fluorescent light; FL-10W, Toshiba). Hunter's colour differences ΔE (L, a, b) accepted by National Bureau of Standard were measured by a colour differences-photometer (Digital colour computer CD-SCH-1: Suga test machine)

The tests were carried out with the tablets prepared by Example A and Reference Example 1 in the same way and under the same conditions as above. The results are shown in the following Table.

TABLE 5

|  | 1 hr | 5 hrs | 10 hrs | 20 hrs | 40 hrs |
|---|---|---|---|---|---|
| sesquihydrate-tablet | 1.0 | 3.4 | 4.9 | 8.0 | 12.5 |
| anhydrate-tablet | 10.3 | 16.2 | 19.2 | 23.0 | 27.2 |

As shown in the above test results the sesquihydrate is extremely superior to the anhydrate and the trihydrate in respect of the stability to light.

(ii) Effect of heat

Each compound (1 g; net weight) was put in a drying chamber keeping at 70°, 50° or 40° C., and the weight of the samples was measured agingly. The results are shown in the following Tables 6, 7 and 8.

TABLE 6

|  | (at 70° C.) | | |
|---|---|---|---|
|  | 1 hr | 3 hrs | 7 hrs |
| sesquihydrate | 0.5% | 1.3 | 1.9 |
| trihydrate | 14 | 14 | 14 |
| anhydrate | 0 | 0 | 0 |

TABLE 7

|  | (at 50° C.) | | |
|---|---|---|---|
|  | 2 hrs | 6 hrs | 10 hrs |
| sesquihydrate | 0% | 0 | 0 |
| trihydrate | 13 | 14 | 14 |
| anhydrate | 0 | 0 | 0 |

TABLE 8

|  | (at 40° C.) | | | |
|---|---|---|---|---|
|  | 2 hrs | 9 hrs | 26 hrs | 50 hrs |
| sesquihydrate | 0% | 0 | 0 | 0 |
| trihydrate | 1.6 | 2.5 | 8.8 | 14.5 |
| anhydrate | 0 | 0 | 0 | 0 |

The numerical figures in the above Tables show a decrease of weight in percentage from the starting weight. As shown in the test results above it is found that the trihydrate decreases its weight equivalent to three molecules of water of crystallization in a short time, whereas the sesquihydrate does not show any change of weight. Therefore, the sesquihydrate is relatively stable to heat as well as the anhydrate.

(iii) Effect of humidity

Each crystal was left in desiccators adjusted to the desired humidities by saturated solution of electrolytes* at 30° C. The changes of weight were measured agingly.

The results are shown in Table 9 on the sesquihydrate, Table 10 on the anhydrate and Table 11 on the trihydrate.

*Relative humidity 90.5%—KNO₃
Relative humidity 75.2%—NaCl
Relative humidity 59.4%—NH₄NO₃
Relative Humidity 46.7%—Ca(NO₃)₂
Relative humidity 0.0%—silicagel

TABLE 9

|  | AT-2266.sesquihydrate | | | |
|---|---|---|---|---|
| relative humidity | one day | 7 days | 21 days | 41 days |
| 90.5% | +1.2% | +1.5 | +1.5 | +1.4 |
| 75.2 | +1.2 | +1.6 | +1.4 | +1.4 |
| 59.4 | +0.2 | +0.5 | +0.5 | +0.6 |
| 46.7 | −0.1 | −0.1 | −0.1 | −0.1 |

TABLE 9-continued

AT-2266.sesquihydrate

| relative humidity | one day | 7 days | 21 days | 41 days |
|---|---|---|---|---|
| 0.0 | −0.2 | −0.2 | −0.2 | −0.3 |

+: increase
−: decrease

TABLE 10

Anhydrous AT-2266

| relative humidity | one day | 2 days | 5 days | 12 days |
|---|---|---|---|---|
| 90.5% | +15.6% | +15.6 | +15.6 | +15.6 |
| 75.2 | +8.9 | +14.8 | +15.5 | +15.2 |
| 59.4 | +4.4 | +11.0 | +14.2 | +15.9 |
| 46.7 | −0.5 | −0.5 | −0.6 | −0.4 |
| 0.0 | 0.0 | 0.0 | −0.1 | −0.1 |

+: increase
−: decrease

TABLE 11

AT-2266.trihydrate

| relative humidity | 2 days | 6 days | 14 days | 28 days |
|---|---|---|---|---|
| 90.5% | 0.0% | +0.2 | +0.2 | +0.2 |
| 75.2 | 0.0 | 0.0 | +0.1 | +0.1 |
| 59.4 | −0.1 | −0.1 | −0.1 | −0.1 |
| 46.7 | −0.2 | −0.3 | −0.1 | −0.1 |
| 0.0 | −5.0 | −9.3 | −14.2 | −14.2 |

+: increase
−: decrease

As shown above, the sesquihydrate does not practically absorb not desorb water in the range from lower to higher humidity. On the other hand, the anhydrate evidently absorbs water under high humidity and the trihydrate releases water under low humidity.

From the results of thermal analysis and X-ray powder diffraction of each compound in the state of equilibrium between absorption and release of water the crystalline anhydrate and the crystalline trihydrate are convertible into each other, but the sesquihydrate is not converted into any form. It is found therefore that the sesquihydrate is not so affected by any change of humidity, whereas the anhydrate and the trihydrate are affected significantly.

(4) Dissolution rate

The dissolution rate of each powdered compound was measured, and the results are shown below.

Test method;

The dissolution tests were carried out with powdered samples, equivalent to 100 mg of the anhydrous AT-2266, in one liter of medium* kept at 37°±2° C. with stirring by two bladed paddle (50 rpm). At regular intervals, 3 ml of the solution was taken. After removal of insoluble material by filtration, 1 ml of filtration was diluted with 9 ml of 0.1 N hydrochloric acid. The dissolution rate of the materials were calculated from measurement of absorption of the solution at 266 nm with $E_{1\ cm}^{1\%} = 1.3 \times 10^3$.

*pH 1.2 solution; The first fluid defined in the disintegration test method in the Japanese Pharmacopoeia (9th Edition)
pH 5 solution; The solution adjusted to pH 5 prepared with the first fluid and the second fluid defined in the disintegration test method in the Japanese Pharmacopoeia (9th Edition)
Preparation method of the first and second fluids;
First fluid: Dissolve 2.0 g of sodium chloride in 24.0 ml of dilute hydrochloric acid and add sufficient water to make 1000 ml. This solution is transparent and colorless and its pH is about 1.2.
Second fluid: Dissolve 35.8 g of disodium hydrogen phosphate in 6.0 ml of dilute hydrochloric acid and add sufficient water to make 1000 ml. This solution is transparent and colorless and its pH is about 7.5.

TABLE 12

Rate of dissolution in water

| | 2 min | 5 min | 10 min | 15 min | 30 min |
|---|---|---|---|---|---|
| sesquihydrate | 72% | 99 | 100 | — | — |
| anhydrate | 1 | 8 | 10 | 15 | 27 |
| trihydrate | 85 | 96 | 98 | 100 | — |

TABLE 13

Rate of dissolution in the pH 5 solution

| | 2 min | 5 min | 10 min | 15 min | 30 min |
|---|---|---|---|---|---|
| sesquihydrate | 85% | 100 | — | — | — |
| anhydrate | 2 | 10 | 14 | 19 | 35 |
| trihydrate | 85 | 98 | 100 | — | — |

TABLE 14

Rate of dissolution in the pH 1.2 solution

| | 2 min | 5 min | 10 min |
|---|---|---|---|
| sesquihydrate | 98% | 99 | 100 |
| anhydrate | 81 | 89 | 94 |
| trihydrate | 89 | 100 | — |

The dissolution rate was also measured with the tablets prepared by Example A and Reference Example 1 according to the method described above. The results are shown below.

TABLE 15

| | | 2 min | 5 min | 10 min | 15 min | 30 min |
|---|---|---|---|---|---|---|
| sesqui-hydrate tablet | water | 44% | 76 | 90 | — | |
| | pH 1.2 solution | 97 | 100 | — | | |
| anhydrate tablet | water | | 11% | 23 | 40 | 70 |
| | pH 12. solution | | 28 | 50 | 68 | 100 |

As shown in the above Table, the sesquihydrate dissolves more rapidly than the anhydrate. In the form of tablets the same tendency is observed.

In addition, the times of disintegration of the tablets containing the sesquihydrate and the anhydrate respectively were measured by the distintegration method for tablets defined in the Japanese Pharmacopoeia, and from the results it is found that the former disintegrates more rapidly than the latter.

(5) Rate of transference into blood

The sesquihydrate, the trihydrate and the anhydrate in the form of capsules were each orally administered to beagle dogs. The blood was collected by vein puncture at regular intervals after administration, and the drug concentration in plasma was measured. From the results it is found that the sesquihydrate is transferred into blood at the same level as the trihydrate, but the sesquihydrate is much more transferred into the blood than the anhydrate.

The antibacterial activities in vitro and in vivo of the sesquihydrate are essentially same with those of the known AT-2266.

Doses of the sesquihydrate of this invention may vary with the age, body weight and conditions of the subjects, the administration route, the number of administrations or the like, but is in the range of 1.7 to 120 mg per kilogram of body weight per day, preferably 3.5 to 80 mg per kilogram of body weight per day, for administration to man. The dose may be divided and administered in two to several times per day. The administration route is preferably oral.

The sesquihydrate of the present invention can be administered as it is, but usually in the form of a pharmaceutical preparation with pharmaceutical acceptable carriers or adjuvants. Specific examples are tablets, capsules, granules, fine granules, powders, etc. These pharmaceutical preparations are prepared in accordance with a customary manner. The adjuvants and carriers are those which are usually used in the field of pharmaceutical preparation and do not react with the compounds of the present invention. These adjuvants and carriers are preferably solid and exemplified by conventional materials such as starch, mannitol, crystalline cellulose, sodium carboxymethylcellulose, or the like.

The pharmaceutical preparation of this invention, for example tablets and capsules, may contain about 10 to about 700 mg, generally 50 to 500 mg of the sesquihydrate of this invention, per tablet or capsule. These amounts are not critical, and may be varied according to whether the required amount of the sesquihydrate of this invention is administered at a time or dividedly.

The present invention is illustrated by the following Examples and Reference Examples.

EXAMPLE 1

The anhydrous AT-2266 (18 g) was left in a humidity oven (70° C., relative humidity 90%) for 20 hours in order to transform the crystalline form, and the resulting crystals were dried at 70°–80° C. for elimination of the adhering water to give the AT-2266.sesquihydrate (20 g). m.p. 220°–224° C.

| Elementary Analysis (as $C_{15}H_{17}N_4O_3F\cdot1.5H_2O$) | | | | |
|---|---|---|---|---|
| | C | H | N | F |
| Calculated Value (%) | 51.87 | 5.80 | 16.13 | 5.47 |
| Found Value (%) | 51.88 | 5.69 | 16.14 | 5.78 |

The crystals were identified as the AT-2266.sesquihydrate from IR spectrum, thermal analysis and X-ray powder diffraction.

EXAMPLE 2

Twenty grams of AT-2266.sesquihydrate was obtained from 22 g of AT-2266.trihydrate in the same way as Example 1.

EXAMPLE 3

About 10 g of anhydrous AT-2266.trihydrate was suspended in water (50 ml) kept at 70° C. with stirring. To the suspension were seeded about 0.1 g of the crystalline AT-2266.sesquihydrate, followed by stirring for about one hour. The resulting crystals were collected by filtration on heating and the crystals were dried for 2 hours for elimination of the adhering water to give the AT-2266.sesquihydrate.

EXAMPLE 4

Ten grams of anhydrous AT-2266 was suspended in water (100 ml) and the suspension was heated at 80° C. with stirring and kept at 80° C. for 20 minutes. The resulting crystals were collected by filtration and dried over anhydrous calcium chloride in a desiccator for one hour to give 10.7 g of the AT-2266.sesquihydrate.

EXAMPLE 5

About 10 g of anhydrous AT-2266 or trihydrate was dissolved into 1.5% aqueous sodium hydroxide (150 ml). The solution was heated to 70° C. and neutralized with 30% acetic acid which was warmed to 70° C. previously. The precipitate was collected by filtration and dried at 70°–80° C. for elimination of the adhering water to give the AT-2266.sesquihydrate.

EXAMPLE 6

AT-2266.trihydrate was sealed in an ampoule and kept at 60° to 62° C. for a week. Wet powders were dried at 70° to 80° C. for elimination of the adhering water to give the AT-2266.sesquihydrate.

EXAMPLE 7

AT-2266.trihydrate was kept at 121° C. in an autoclave for an hour. Wet powders were dried at 70° to 80° C. for elimination of adhering water to give the AT-2266.sesquihydrate.

EXAMPLE 8

AT-2266.trihydrate or anhydrate was kept in a chamber into which vapor steam (about 110° C.) was blown for an hour. Wet powders were dried at 70° to 80° C. for elimination of adhering water to give the AT-2266.sesquihydrate.

EXAMPLE 9

About 10 g of AT-2266.hydrochloride was dissolved to hot water (about 70° C.) and the solution was neutralized with 15% aqueous solution of sodium hydroxide which was warmed to 70° C. previously. The precipitate was collected by filtration and dried at 70° to 80° C. for elimination of adhering water to give the AT-2266.sesquihydrate.

EXAMPLE 10

AT-2266.anhydrate (20 g: 60.8 m moles) and water (1.7 g: 94.4 m moles) were sealed in an ampoule and kept at 70° C. for 24 hours to give the AT-2266.sesquihydrate.

EXAMPLE 11

AT-2266.trihydrate was left in a humidity oven (70° C., relative humidity 30%) for 4 weeks in order to transform the crystalline form, and the resulting crystals were dried at 70°–80° C. for elimination of the adhering water to give the AT-2266.sesquihydrate.

EXAMPLE 12

AT-2266.trihydrate was sealed in an ampoule and kept at 160° C. for an hour. Wet powders were dried at 70° to 80° C. for elimination of the adhering water to give the AT-2266.sesquihydrate.

EXAMPLE A

The AT-2266.sesquihydrate (217 g), corn starch (108 g), calcium carboxymethylcellulose (10 g) and hydroxypropylcellulose (5 g) were kneaded together with water. The mixture was dried at 60° C. and screened. The granules were further mixed with magnesium stearate (7 g) and light anhydrous silicic acid (3 g) to give granules for tableting. The granules were compressed into tablets each having a weight of 175 mg and containing 108.5 mg of AT-2266.sesquihydrate.
hardness: 11 kg disintegration times:
1 min (water)
2 min (1st fluid)

EXAMPLE B

AT-2266.sesquihydrate (217 g), lactose (88 g), corn starch (88 g) and magnesium stearate (7 g) were mixed to give powders. The powders were filled up into capsules (No. 3) to give capsules each containing 200 mg of AT-2266.sesquihydrate.
disintegration time: 10 min (water)

EXAMPLE C

In a pony mixer, AT-2266.sesquihydrate (108 g), lactose (400 g), corn starch (462 g) and hydroxypropylcellulose (30 g) were kneaded together with water. The mixture was formed into granules using ECK pelleter with screen diameter 0.45 mm (Fuji Powdal). After drying at 60° C. the granules were screened with a twin rotor to give fine granules containing the AT-2266.sesquihydrate.

EXAMPLE D

By coating tablets prepared by Example A with hydroxypropylcellulose, there were obtained film-coated tablets containing the AT-2266.sesquihydrate.

REFERENCE EXAMPLE 1

The anhydrous AT-2266 (200 g), corn starch (130 g), calcium carboxymethylcellulose (10 g) were kneaded together with water. After drying in air-fluidized bed at 60° C. the mixture was screened. To the granules were added magnesium stearate (7 g), light anhydrous silicic acid (3 g) to give granules. The granules were compressed into tablets each weighing 175 mg containing 100 mg of anhydrous AT-2266.
hardness: 11.2 kg
disintegration times:
30 min (water)
20 min (1st fluid)

REFERENCE EXAMPLE 2

2,6-Dichloro-3-nitropyridine was reacted with N-ethoxycarbonylpiperazine to give 6-chloro-2-(4-ethoxycarbonyl-1-piperazinyl)-3-nitropyridine. The product, without purification, was heated with ethanolic ammonia in an autoclave at 120°–125° C. to give 6-amino-2-(4-ethoxycarbonyl-1-piperazinyl)-3-nitropyridine (mp 132°–134° C.), which was treated with acetic anhydride in acetic acid to give 6-acetylamino-2-(4-ethoxycarbonyl-1-piperazinyl)-3-nitropyridine (mp 168°–169° C.). This compound was catalytically hydrogenated in the presence of 5% palladium-carbon in acetic acid to yield 3-amino-6-acetylamino-2-(4-ethoxycarbonyl-1-piperazinyl)pyridine. The obtained 3-amino derivative, without further purification, was dissolved in a mixture of ethanol and 42% tetrafluoroboric acid, and to this solution was added a solution of isoamyl nitrite in ethanol at below 0° C. with stirring. Twenty minutes later, ether was added to the solution. The resulting precipitate was collected by filtration and washed with a mixture of methanol and ether and then with chloroform to yield 6-acetylamino-2-(4-ethoxycarbonyl-1-piperazinyl)-3-pyridine diazonium tetrafluoroborate; mp 117°–117.5° C. (dec.).

A suspension of the diazonium salt in toluene was gradually heated and kept at 120° C. (bath temp.) for 30 minutes with stirring. After evaporation of the solvent under reduced pressure, the residue was made alkaline with 10% sodium carbonate and then extracted with chloroform. The chloroform extract was dried over anhydrous potassium carbonate. After evaporation of the solvent, the crystalline residue was recrystallized from ethyl acetate to give 6-acetylamino-2-(4-ethoxycarbonyl-1-piperazinyl)-3-fluoropyridine (mp 132°–133° C.).

The 3-fluoro derivative was hydrolyzed with a mixture of 15% hydrochloric acid and methanol (1:2 v/v) to give 6-amino-2-(4-ethoxycarbonyl-1-piperazinyl)-3-fluoropyridine. This compound was treated with diethyl ethoxymethylenemalonate at 130°–140° C. to give diethyl N-[2-(4-ethoxycarbonyl-1-piperazinyl)-3-fluoro-6-pyridinyl]aminomethylenemalonate (mp 144°–145° C.) and then the product was cyclized by heating at 255° C. to give ethyl 7-(4-ethoxycarbonyl-1-piperazinyl)-6-fluoro-1,4-dihydro-4-oxo-1,8-naphthyridine-3-carboxylate (mp 279°–281° C.).

The carboxylate (1.0 g) was suspended in dimethylformamide (10 ml) and to the suspension was added potassium carbonate (0.53 g). After the mixture was kept at 60° C. for 10 minutes with stirring, ethyl iodide (1.2 g) was added to the solution. The mixture was stirred for 2 hours at 60°–70° C. The reaction mixture was concentrated to dryness under reduced pressure, and water was added to the residue. After extraction with chloroform, the chloroform extract was dried over anhydrous potassium carbonate. After removal of the chloroform by distillation under reduced pressure, the resulting precipitate was recrystallized from a mixture of dichloromethane and n-hexane to give 0.89 g of ethyl 1-ethyl-6-fluoro-1,4-dihydro-4-oxo-7-(4-ethoxycarbonyl-1-piperazinyl)-1,8-naphthyridine-3-carboxylate (mp 171°–173° C.).

A mixture of the above ethyl ester (0.8 g), 10% sodium hydroxide (6 ml) and ethanol (2 ml) was refluxed by heating for 3 hours. After cooling, the solution was adjusted to pH 7.0–7.5 with 10% acetic acid. The precipitate was collected by filtration, washed with ethanol, recrystallized from a mixture of dimethylformamide and ethanol and dried at 110° C. to give the anhydrous AT-2266 [1-ethyl-6-fluoro-1,4-dihydro-4-oxo-7-(1-piperazinyl)-1,8-naphthyridine-3-carboxylic acid], mp 220°–224° C.

| Elementary analysis (as $C_{15}H_{17}N_4O_3F$): | | | |
|---|---|---|---|
| | C | H | N | F |
| Calculated Value (%): | 56.24 | 5.35 | 17.49 | 5.93 |
| Found Value (%): | 56.06 | 5.32 | 17.62 | 5.93 |

The crystals were identified as the anhydrous AT-2266 from IR spectrum, thermal analysis and X-ray powder diffraction.

REFERENCE EXAMPLE 3

The anhydrous AT-2266 prepared by Reference Example 2 was suspended in water and the suspension was stirred at room temperature. The resulting crystals were collected by filtration and dried at 35° C. for elimination of the adhering water to give the AT-2266.trihydrate, mp 220°–224° C.

| Elementary analysis (as $C_{15}H_{17}N_4O_3F \cdot 3H_2O$): | | | |
|---|---|---|---|
| | C | H | N | F |
| Calculated Value (%): | 48.12 | 6.19 | 14.97 | 5.08 |

| Elementary analysis (as $C_{15}H_{17}N_4O_3F \cdot 3H_2O$): | | | | |
|---|---|---|---|---|
| | C | H | N | F |
| Found Value (%): | 48.09 | 6.04 | 14.95 | 5.36 |

The crystals were identified as the AT-2266.trihydrate from IR spectrum, thermalanalysis and X-ray powder diffraction.

REFERENCE EXAMPLE 4

The anhydrous AT-2266 prepared by Reference Example 2 or the AT-2266.trihydrate prepared by Reference Example 3 was dissolved in 5% hydrochloric acid and the solution was concentrated to dryness under reduced pressure. The residue was recrystallized from water to give the AT-2266.hydrochloride, mp above 300° C. (dec.).

REFERENCE EXAMPLE 5

The anhydrous AT-2266 prepared by Reference Example 2 or the AT-2266.trihydrate prepared by Reference Example 3 was dissolved in 7% methanesulfonic acid solution on heating. After cooling, the precipitate was recrystallized from diluted methanol to give a methanesulfonic acid salt of the AT-2266, mp. above 300° C. (dec.).

What we claim is:

1. 1-Ethyl-6-fluoro-1,4-dihydro-4-oxo-7-(1-piperazinyl)-1,8-naphthyridine-3-carboxylic acid.sesquihydrate.

2. A method for treatment of a bacterial infectious disease which comprises orally administering to a warm-blood animal an effective dose of the sesquihydrate defined in claim 1.

3. A process for the preparation of 1-ethyl-6-fluoro-1,4-dihydro-4-oxo-7-(1-piperazinyl)-1,8-naphthyridine-3-carboxylic acid.sesquihydrate which comprises heating 1-ethyl-6-fluoro-1,4-dihydro-4-oxo-7-(1-piperazinyl)-1,8-naphthyridine-3-carboxylic acid at a temperature above about 60° C. in the presence of water in an amount sufficient to form the sesquihydrate.

4. A process according to claim 3 which comprises heating 1-ethyl-6-fluoro-1,4-dihydro-4-oxo-7-(1-piperazinyl)-1,8-naphthyridine-3-carboxylic acid.trihydrate at a temperature above about 60° C. in the presence of water.

5. A process according to claim 3 which comprises heating 1-ethyl-6-fluoro-1,4-dihydro-4-oxo-7-(1-piperazinyl)-1,8-naphthyridine-3-carboxylic acid.anhydrate at a temperature above about 60° C. in the presence of water in an amount sufficient to form the sesquihydrate.

6. A process according to claim 3 which comprises heating anhydrate and/or trihydrate of 1-ethyl-6-fluoro-1,4-dihydro-4-oxo-7-(1-piperazinyl)-1,8-naphthyridine-3-carboxylic acid at a temperature above about 60° C. and a relative humidity above 30%.

7. A process according to claim 6 which is carried out under a relative humidity above 80%.

8. A process according to claim 3 which comprises suspending anhydrate and/or trihydrate of 1-ethyl-6-fluoro-1,4-dihydro-4-oxo-7-(1-piperazinyl)-1,8-naphthyridine-3-carboxylic acid in water and heating the suspension at a temperature above about 60° C.

9. A process according to claim 3 which comprises dissolving anhydrate and/or trihydrate of 1-ethyl-6-fluoro-1,4-dihydro-4-oxo-7-(1-piperazinyl)-1,8-naphthyridine-3-carboxylic acid in an aqueous alkaline solution or aqueous acidic solution, and neutralizing the solution by addition of an acid or alkali, and keeping it at a temperature above about 60° C.

10. A process according to claim 3 which comprises dissolving a salt of 1-ethyl-6-fluoro-1,4-dihydro-4-oxo-7-(1-piperazinyl)-1,8-naphthyridine-3-carboxylic acid in water, and neutralizing the solution by addition of an acid or alkali, and keeping it at a temperature above 60° C.

11. An antibacterial composition comprising as an active ingredient an antibacterially effective amount of the sesquihydrate defined in claim 1 and a pharmaceutically acceptable carrier therefor.

* * * * *